United States Patent
Call (10) Patent No.: US 6,218,669 B1
(45) Date of Patent: Apr. 17, 2001

(54) SURGICAL PROBE APPARATUS

(75) Inventor: John D. Call, Columbus, OH (US)

(73) Assignee: Neoprobe Corporation, Dublin, OH (US)

( * ) Notice: Subject to any disclaimer, the term of this patent is extended or adjusted under 35 U.S.C. 154(b) by 0 days.

(21) Appl. No.: 09/167,420

(22) Filed: Oct. 6, 1998

(51) Int. Cl.⁷ .................................................. G01T 1/161
(52) U.S. Cl. ................................ 250/370.11; 250/336.1; 250/370.01
(58) Field of Search ........................... 250/336.1, 370.01, 250/370.11

(56) References Cited

U.S. PATENT DOCUMENTS

| | | |
|---|---|---|
| 4,782,840 | 11/1988 | Martin et al. . |
| 4,801,803 | 1/1989 | Denen et al. . |
| 4,889,991 | 12/1989 | Ramsey et al. . |
| 4,893,013 | 1/1990 | Denen et al. . |
| 5,036,201 | 7/1991 | Carroll et al. . |
| 5,070,878 | 12/1991 | Denen . |
| 5,151,598 | 9/1992 | Denen . |
| 5,441,050 | 8/1995 | Thurston et al. . |
| 5,475,219 | 12/1995 | Olson . |
| 5,732,704 | 3/1998 | Thurston et al. . |

OTHER PUBLICATIONS

Morton, et al., "Technical Details of Intraoperative Lymphatic Mapping for Early Stage Melanoma, " *Arch Surg.* 1992 127: 392–399.

Uren, et al., "Lymphoscintigraphy in High–Risk Melanoma of the Trunk: Predicating Draining Node Groups, Defining Lymphatic Channels and Locating the Sentinel Node," *T Nucl Med.* 1993 34:1435–1440.

"Lymphatic Mapping and Sentinel Lymphadenectomy for Breast Cancer," *Annals of Surg.* vol. 220, No. 3:391–401 1994 J.B. Lippincott Company.

*Primary Examiner*—Constantine Hannaher
*Assistant Examiner*—Andrew Israel
(74) *Attorney, Agent, or Firm*—Mueller and Smith LPA (57) ABSTRACT

A surgical probe apparatus incorporates a probe structure with a handle component and forward crystal mount wherein a cadmium-telluride crystal is rigidly mounted against movement. A cup-shaped window assembly is provided having an internal cylindrical tungsten shield which extends forwardly from the front face of the crystal to define an air gap as well as to support an aluminum window. The window assembly is threadably mounted upon the handle at a transition region forming an outwardly extending ramp. This ramp is used in conjunction with a polymeric retainer component with legs containing dog structures which hold a cylindrical tungsten collimator in biased position against the window when attached.

20 Claims, 8 Drawing Sheets

SURGICAL PROBE APPARATUS

CROSS-REFERENCE TO RELATED APPLICATIONS

STATEMENT REGARDING FEDERALLY SPONSORED RESEARCH

Not applicable.

BACKGROUND OF THE INVENTION

The involvement of the lymph system in tumor metastasis has been the subject of extensive investigation and is well established. Lymphatic systems are present as widely dispersed tissues, fluids, and cells concerned in a variety of interrelated functions of the mammalian body including the circulation and modification of tissue fluid formed in the capillary beds, and the removal by mononuclear phagocytes of cell debris and foreign matter. The lymphatic system is importantly involved in participation with the blood vascular system in developing the immune response of die lymphocytes and other cells. Lymph flows within the system as a consequence of a variety of perceived mechanisms of organ and tissue dynamics. For certain cancers, metastasis occurring in consequence of lymph drainage will result in an initial location or positioning of neoplastic cells at certain lymph nodes typically deemed "regional nodes" within a pertinent lymph drainage basin. Some cancers, for example, melanomas, have been observed to exhibit variability in lymphatic drainage patterns emanating from different portions of the body. Other cancers, such as those encountered in the breast, will evidence somewhat more predictable nodal involvement. In designing forms of cancer disease management, therefore, efforts are directed to the identification of affected lymph nodes. For melanomnas, it has been a more recent practice to identify the pertinent drainage basin or regional nodes along with an evaluation of the extent of lymph involvement with micrometastasis. A presurgical step undertaken in about 20% of investigational procedures concerning melanomas looks to carrying out of a gamma camera generated form of lymphoscintigraphy which gives the clinician a gross two-dimensionally limited image, generally showing the tumor site injection of sulfur colloid labeled with Technetium 99-m ($^{99m}$Tc) and, spaced therefrom, a region of radioactivity at the pertinent regional lymph nodes. The latter information at least confirms the path of drainage and the location of the proper drainage basin. Regional nodes then are removed and submitted for pathology evaluation.

For cancers such as breast cancer, the sites of lymph node involvement are commonly encountered at axillary, internal mammary, and supraclavicular lymph node regions. Of these, the axillary lymph node region is the principal site of regional metastasis from carcinoma of the breast, and approximately 40% of patients have evidence of spread to the axillary nodes. In early approaches to the disease, these axillary nodes were removed as a form of therapy. Presently, however, their positive involvement, or lack thereof, has become the subject of diagnostics as opposed to therapy. In this regard, the combination of the presence and extent of metastasis to the axilla represents the single most important prognostic factor for the management of patients with breast cancer. See generally "Cancer, Principles and Practice of Oncology," vol. 1, 4th ed. DeVita, Jr., et al., chapter 40, Harris, et al., J.P. Lippincott Co., Philadephia, Pa. (1993).

The axilla is a triangular region bounded by the axillary vein superiorly, the latissimus dorsi laterally, and the serratus anterior medially. With more current diagnostic procedures, essentially all axillary nodes at the axilla assumed to represent the drainage basin are removed during surgery for analysis. In general, somewhere between 10 and 30 nodes will be removed in the course of dissection with, of course, the attendant risks. In this regard, these nodes are generally surrounded by investment or fatty tissue and visualization of them necessarily is limited. Such dissection will pose risks of cutting the long thoracic nerve, the thoracic-dorsal nerve, the nerve to the pectoralis major or the axillary vein. Morbidity may occur in some cases due to regional node removal and patients are frequently known to discuss a numbing of the arm region following the procedure.

While this form of somewhat radical axillary lymph node dissection has been the conventional approach to determining nodal metastatic involvement, more recent data suggests that less radical axillary node evaluation procedures may generate equivalent information for staging and patient management, but with far more limited dissection and resultant trauma, as discussed below.

Patient management for staging purposes for the case of cutaneous melanoma is highly predicated upon determinations of lymph involvement. A number of factors are involved in the prognosis of the disease, including, inter alia, location, tumor thickness, level of invasion, growth patterns, and of particular importance the identification of regional node metastatic involvement. Generally, surgical excision of metastatic nodes within the drainage basin of a lesion has been considered the only effective treatment for cure or disease control. Some investigators have preferred to excise only clinically demonstrable metastatic nodes associated with the lesion, while others have chosen to excise the nodes even where they may appear normal because of the risk of the presence of occult (clinically undetectable) metastasis. A substantial dialog has been carried on by investigators as to whether or not elective lymph node dissection, or lymphadenectomy, is an appropriate therapy. Elective lymphodenectomy has the major advantage of treating a nodal metastasis at a relatively early stage in its natural history when the tumor burden is low. On the other hand, such an approach may subject patients to surgery which would otherwise have been unnecessary. In particular, where patients exhibit a clinical Stage I level of the disease, there will be no nodal metastasis present and no benefit then can be realized from regional lymphadenectomy.

Morton, et al., undertook an investigation of a procedure designed to identify that lymph node nearest the site of a melanoma and within the pertinent lymph drainage basin. Such a node, being on the most direct drainage pathway will present the most likely site of early metastasis and is referred to as the "sentinel node." Thus, by carrying out only a limited dissection specific to this node and performing pathologic analysis of it, staging can be achieved without at least initial resort to more radical lymphadenectomy. With the approach, once the drainage basin from a lesion is identified, for example, by lymphoscintigraphy, an intraoperative mapping of the cutaneous lymphatics with vital dye is carried out at the time of surgical removal of the primary lesion. The vital dye, for example of blue color, is injected at the site of the lesion and tracked by blunt dissection until the sentinel node is reached. That node is now exclusively of blue color and readily identified. Thus, the sentinel draining lymph node of each primary melanoma is isolated and removed. By examining the sentinel nodes, for example by frozen section using routine hematoxylin-eosin histopathological techniques, as well as rapid immunohistochemical techniques, only those patients who have evidence of micrometastasis in the sentinel draining node are subject to subsequent lymphodenectomy. See generally, Morton D., Wen D-R, Wong J., et al. "Technical Details of Intraoperative Lymphatic Mapping for Early Stage Melanoma," *Arch. Surg.* 1992: 127:392–399; and R. F. Uren, et. al, "Lymphoscintigraphy in High-Risk Melanoma of the Trunk: Predicting Draining Node Groups, Defining Lymphatic Channels and Locating the Sentinel Node," *J. Nucl Med* 1993; 34:1435–1440.

The approach of Morton, et al., also has been undertaken to moderate the otherwise somewhat radical axillary lymph node dissection common in staging breast cancer. Through the utilization of the noted vital dyes in conjunction with the lymph drainage system from primary breast tumor, less radical sentinel node based procedures may result in adequate axillary staging and regional control. With the procedure, in general, a vital blue dye is injected into the breast mass and surrounding breast parenchyma. Following a relatively short interval, a transverse incision is made just below the hair bearing region of the axilla. Blunt dissection is performed until a lymphatic tract or duct leading to a blue stained node is identified. The lymph duct, having a blue color, provides a guide path leading to the location of the most proximal lymph node and thus the sentinel node. This sentinel node is excised and evaluated. While the procedure calls for considerable surgical experience and talent associated with the delicate task of following the blue duct (a ruptured dye-carrying duct can be problematic), the ability to identify a tumor-free sentinel lymph node will enable the surgeon to accurately stage metastasis-free breast cancer patients without subjecting them to the risks of radical dissection. The approach may also improve histologic staging by enabling the pathologist to focus on fewer lymph nodes. See generally Guiliano, A. E.; Kirgan, B. M.; Guenther, J. M.; and Morton, D. L., "Lymphatic Mapping and Sentinel Lymphadenectomy for Breast Cancer," *Annals of Surgery*, vol. 220, no. 3: 391–401, 1994, J. B. Lippincott Company.

As a replacement for or an adjunct to the tracking of portions of the lymph system to locate a sentinel lymph node, practitioners have injected the noted sulfur colloid labeled with $^{99m}$Tc technician at the site of the lesion. Then, employing a hand-held radiation detecting probe, migration of the injectate along the lymph ducts to the sentinel node is carried out. Thurston, et.al, in U.S. Pat. No. 5,732,704 entitled "Radiation Based Method for Locating and Differentiating Sentinel Nodes," issued Mar. 31, 1998, describe an improved technique for thus tracking a lymph duct and for utilizing a thresholding procedure three-dimensionally finding a sentinel lymph node containing a radiopharmaceutical with a hand-held probe. An improved apparatus and system for carrying out this procedure is described by Thurston and Olson in an application for U.S. patent Ser. No. 08/543,032 filed Oct. 13, 1995 and entitled "Remotely Controlled Apparatus and System for Tracking and Locating a Source of Photo Emissions."

Clinical experience with the use of a radiopharmaceutical containing $^{99m}$Tc for locating sentinel nodes has uncovered technical challenges. For hand-held probe detectors employing the desirable compound semiconductor crystal, cadmium-zinc-telluride, the relatively higher gamma energy of $^{99m}$Tc has resulted in marginal performance where the detector crystals were structured and operated in conventional fashion. Such marginal performance has been alleviated by structuring the probe devices, associated crystals and control circuitry to operate in a trapping dependent mode wherein a trapping of substantially all carriers occurs within the volume of the semiconductor. See in this regard, application for U.S. patent Ser. No. 09/167,008 by Thurston entitled "Radiation Probe With Compound Semiconductor Crystal Performing In A Trapping-Dependent Operational Mode" filed Oct. 6, 1998 and assigned in common herewith.

Use of radiation detecting probes also has been burdened by the relatively large deposit of the $^{99m}$Tc based radiopharmaceutical at lesion locations somewhat near to the lymph drainage region. In this regard, breast tumor typically will be close to the location of the sentinel node, for example, within about five inches in many cases. This relatively close proximity creates radiation background interference at the site of the sentinel node, for instance involving Compton scattering phenomena and the like, making identification of the node of interest more difficult.

BRIEF SUMMARY OF THE INVENTION

The present invention is addressed to a surgical probe apparatus which includes a probe mount component structured to support a crystal detector in a rigid, isolated manner in avoidance of crystal induced and electrical noise. Suited for the employment of cadmium-telluride crystal detectors, this rigid support accommodates for the piezoelectric attributes of the compound semiconductors. The rigidity achieved also avoids electrical noise induced by the relative movement of electrical bias carrying components with respect to adjacent grounded structures. Utilizing a cylindrical side shield formed as a component of a cup-shaped window assembly, the mounting structure supporting the detector crystal is isolated by a gap from the forward sidewalls of the probe. This shield component is formed of a structurally robust, radiation attenuating material such as tungsten and functions as a mechanical shield; a side impinging radiation shield; and a structural buttressing component of the probe window, enhancing its performance with a removable collimator. The latter features are found quite useful for probe applications wherein sentinel lymph nodes are located which are situated in relatively close proximity to the site of injection of a radiopharmaceutical.

The structuring, incorporating a rigid mount component and cup-shaped window assembly incorporating a tungsten side shield, also provides the advantage that the probe is readily repaired, for example, following being dropped in the course of its use.

Other objects of the invention will, in part, be obvious and will, in part, appear hereinafter. The invention, accordingly, comprises the apparatus possessing the construction, combination of elements and arrangement of parts which are exemplified in the following description.

For a fuller understanding of the nature and objects of the invention, reference should be had to the following detailed description taken in connection with the accompanying drawings.

DETAILED DESCRIPTION OF THE INVENTION

The probe apparatus and system of the present invention makes advantageous use of an adjunct control system associated with a hand-held probe-based procedure now known as radioimmunoguided surgery (RIGS®) (RIGS being a registered trademark of Neoprobe Corporation of Dublin Ohio). With the RIGS system, a radiolabeled antibody is systemically injected into the patient. The radiolabeled antibody employed is capable of remaining bound to or associated with neoplastic tissue including occult tissue for extended periods of time with the radio tag still bound thereto. By waiting an appropriate interval, even though the accretion of radioactivity at the occult tumor sites decreases over time, the blood pool background and surrounding tissue (relative to the tumor sites) decrease at a much greater rate so that the radioactive sites can be determined readily utilizing the hand-held probe. The seminal patent concerned with the RIGS procedure is U.S. Pat. No. 4,782,840 by Martin and Thurston, entitled "Method For Locating, Differentiating, And Removing Neoplasms," issued Nov. 8, 1988 and assigned in common herewith.

The hand-held probe and preamplification electronics mounted within it in support of a cadmium-zinc-telluride crystal have been the subject of extensive scientific development. Cadmium-zinc-telluride crystals are somewhat fragile and exhibit piezoelectric properties, which, without rigorous accommodation, will produce deleterious noise phenomena and the like. The RIGS system utilizes a relatively lower energy radionuclide, i.e. $^{125}$I (27–35 Kev). In general, the radiolabeled antibody is referred to as a "locator" and only a very small amount of that radioactive locator will be associated with minute, occult tumor sought to be detected. Thus, radiation emission count rates measured with the RIGS system are relatively low. Research activity concerning the above operational criteria is reflected in the following U.S. patents:

U.S. Pat. No. 4,801,803 by Denen, Thurston and Ramsey, entitled "Detector and Localizer for Low Energy Radiation Emissions," issued Jan. 31, 1989.

U.S. Pat. No. 4,893,013 by Denen, Thurston and Ramsey, entitled "Detector and Localizer for Low Energy Radiation Emissions," issued Jan. 9, 1990.

U.S. Pat. No. 5,070,878 by Denen, entitled "Detector and Localizer for Low Energy Radiation Emissions," issued Dec. 10, 1991.

U.S. Pat. No. 5,151,598 by Denen, entitled "Detector and Localizer for Low Energy Radiation Emissions," issued Sep. 29, 1992.

To derive data representing the presence or absence of occult tumor, a microprocessor-driven complex system of analysis continuously works to statistically evaluate validated counts or gamma strikes to aurally apprise the surgeon of the presence or absence of occult neoplastic tissue. An algorithm under which the noted evaluation takes place is described in U.S. Pat. No. 4,889,991 by Ramsey and Thurston, entitled "Gammna Radiation Detector With Enhanced Signal Treatment," issued Dec. 26, 1989 and assigned in common herewith. An adjunct system combined with the RIGS system which is utilized in conjunction with the radiopharmaceutical $^{99m}$Tc is described in application for United States patent by Call, entitled "System For Locating And Detecting A Source Of Photon Emissions" filed Oct. 4, 1997, Ser. No. 08/944,078. That adjunct control system, as combined with the forward components of the control circuitry of the RIGS system, is used in connection with the system and apparatus of the present invention.

Cadmium-telluride crystals may be alloyed, for example, with zinc and, for the present description, still are referred to as "Cadmium-telluride" or "CdTe." A preferred cadmium telluride crystal as described in commonly-assigned U.S. Pat. No. 5,441,050, issued Aug. 15, 1995 is cadmium-telluride material alloyed with zinc. The proportioning of the cadmium component and zinc component of the crystals may vary to provide an effective ratio selected to suit the particular requirement of the user.

Figure 1:
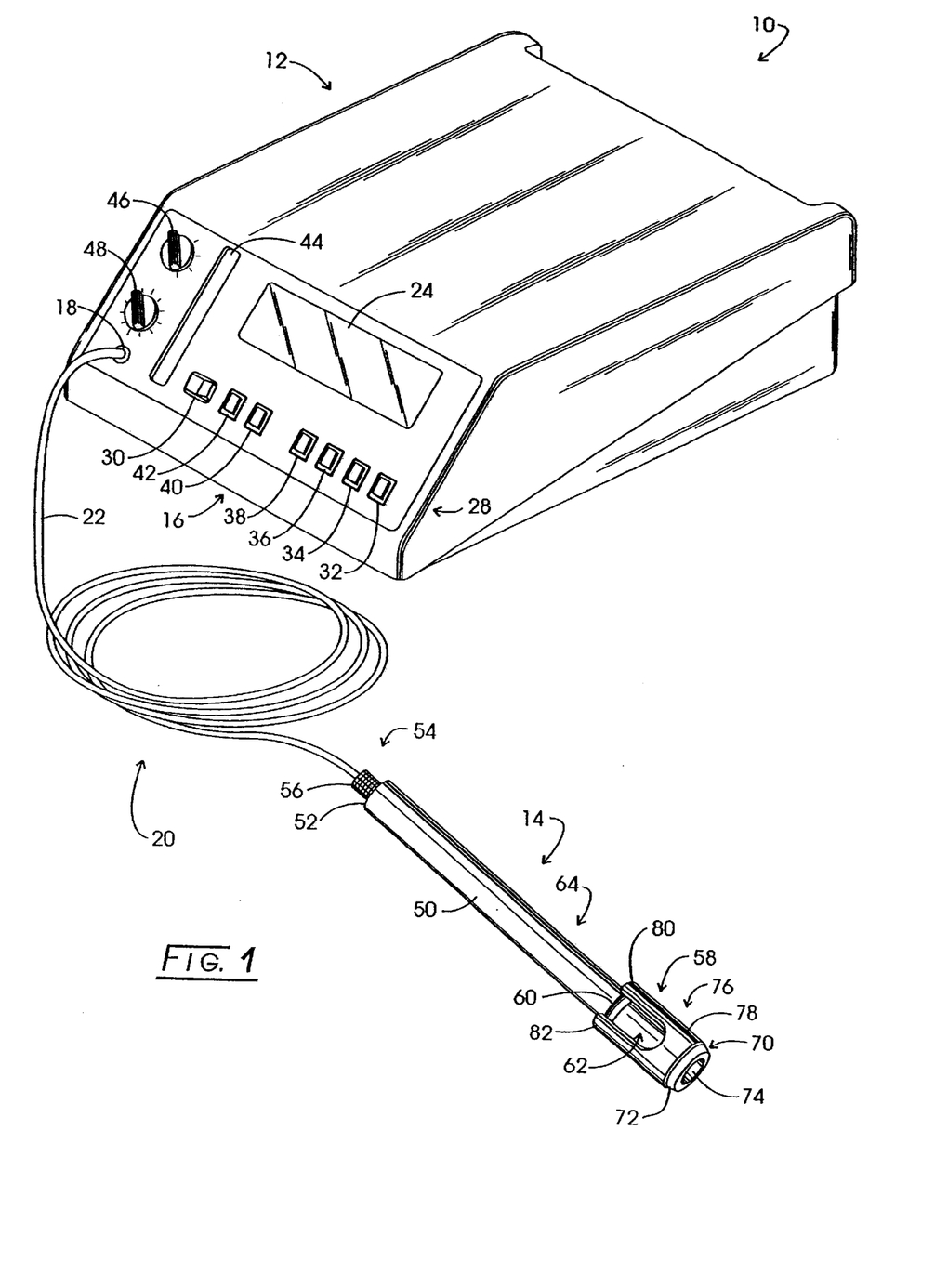
FIG. 1 is a pictorial representation of the system and instrumentation of the invention.

Referring to FIG. 1, surgical apparatus and system for alternately locating and differentiating relatively low gamma energy radionuclides, as well as a relatively high gamma energy, non-systemically injected as radiophanmaceutical is represented generally at 10. System 10 includes a control assembly or console 12 to which is coupled a probe or probe apparatus represented generally at 14. The control console 12 is configured for both carrying out radioimmunoguided surgery and for tracking radiopharmaceutical injected at the situs of tumor to locate a lymph sentinel node. In the latter regard, the photon count evaluation, including lower threshold and upper limit windowing functions of the RIGS system are commonly utilized. Such a RIGS system is described, for example, in U.S. Pat. No. 4,801,803 by Denen, Thurston and Ramsey, entitled "Detector and Localizer for Low Energy Radiation Emissions" issued Jan. 31, 1989. The forward face 16 of console 12 includes a coupling or connector 18 which provides for electrical signal communication and power supply association with the probe apparatus 14 via a transmission assembly represented generally at 20 which includes a flexible cable 22. This cable implementation of the transmission assembly is a preferred arrangement for such transmission function, however, other approaches will occur to those skilled in the art. Forward face 16 of console 12 additionally carries a relatively large liquid crystal display (LCD) readout 24, as well as an array of push-type switches 28. This array of switches 28 permits the microprocessor driven control assembly 12 to carry out an instructive or "user friendly" dialog with the practitioner. In addition to a conventional on and off rocker switch 30, the switches provided at forward face 16 include such function selection switches as a count mode switch 32, a reset count switch 34, a background count or squelch switch 36, a sound control switch 38, and down and up incrementing switches shown, respectively at 40 and 42. Also mounted at the forward face 16 of console 12 are components dedicated to the lymph tracking features of the system 10. In this regard, a linear, segmented LED array 44 is included for the purpose of providing a visual cueing aspect as to peak count rate level. A range selection switch is provided at 46. Switch 46 permits the practitioner to select any of five count rate ranges to achieve full-scale readout. These ranges may, for example, be 0–100 counts per second; 20–1,000 counts per second; 50–2,500 counts per second; 100–7,500; and 600–30,000 counts per second. Below the knob actuated range switch 46 is a knob actuated threshold control 48 which is used to provide a count rate threshold input which is a percentage valuation of any one of the count ranges established at switch 46. This thresholding is a variation of how the background count or "squelch" procedure is carried out in connection with switches 36 and 34. In this regard, the function of reset count switch 34 is to derive a count value over a preset interval, for example, two seconds. The background count switch 36 is employed in conjunction with reset count switch 34 to develop a statistical count value based upon a measured background count rate. The microprocessor based control system of console 12 then calculates a statistically significant value, for example, a predetermined number of standard deviations of the basic background count rate to derive a statistically significant threshold radiation count level. This, for example, may be three sigma above the base count rate. The ranging procedure is referred to by surgeons as "squelching." Operating in conjunction with that threshold level in the RIGS procedure, the system 10 provides the surgeon with audible cues indicating that a high probability of tumor involvement is present at a location closely adjacent to the position of the forward window of a hand-held probe employed for this procedure. A "squelching" procedure may also be utilized in conjunction with the detecting and locating of sentinel lymph nodes. However, with the system 10, a dedicated adjunct system is provided for that purpose as is the probe apparatus 14. Positioned at the rear of console 12 is a mode selection switch (not shown) which is manually actuated to either of two positions, one electing that the system 10 operate in its standard RIGS mode, and the other electing that system 10 operate in conjunction with the adjunct system for carrying out sentinel node detection.

Probe 14 is seen to be configured having a generally cylindrically shaped handle component 50. Cable 22 is connected in electrical association with the handle component 50 at the rearward end 52 thereof utilizing a connector assembly 54, the component 56 of which is permanently attached to cable 22. Handle component 50 extends from the rearward end 52 to a forward region represented generally at 58 which commences at an annular transition portion 60. Disposed over the forward region 58 of the handle component 50 is a cup-shaped window assembly represented generally at 62.

Removably positioned over the window assembly 62 is a collimator assembly represented generally at 70. The assembly includes a right cylindrical collimator 72 having an open cylindrical interior surface extending to the window assembly 62. Collimator 72 is formed of a material attenuating radiation such as tungsten. Attached to the collimator 72 is a polymeric retainer component represented generally at 76 which is formed having a forward portion 78 integrally formed with two resilient rearwardly disposed leg portions 80 and 82, the tips of which are configured to resiliently engage the transition portion 60 of handle component 50. The collimator assembly 70 has particular value during procedures for locating a sentinel node where the radiopharmaceutical injectate is relatively close to the location of that sentinel node by virtue of its blocking transversely directed radiation, including Compton scattering phenomena.

Figure 2:
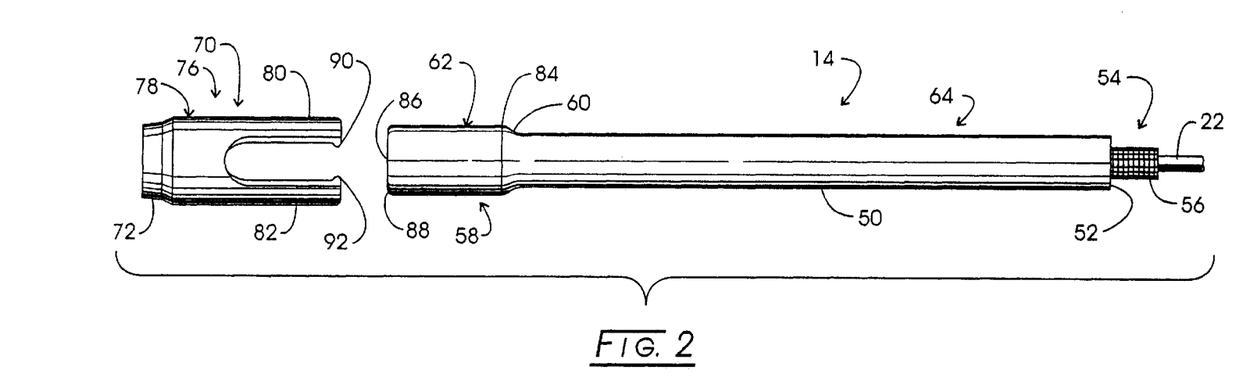
FIG. 2 is a side view of the probe apparatus shown in FIG. 1 with a collimator assembly detached from the probe component.

Referring to FIG. 2, assembly 14 is shown with the collimator assembly 70 removed from the uncollimated probe represented generally at 64. The figure reveals an interface represented at interface line 84 between the transition region 60 and the window assembly 62. Additionally, the assembly 62 includes a radiation transmissive forward looking window 86. Note that the forward edge of window 86 is configured having a curvature or is rounded off at 88.

Looking again to the collimator 70, it may be observed that resilient leg portion 80 is configured to have an inwardly depending dog 90. Integrally formed with the leg 80, the dog 90 has a curvature corresponding with the curvature of the handle component 50 adjacent the transition region 60. A similar curved dog 92 is integrally formed with resilient leg 82. The term "dog," as used herein, is intended to mean any resiliently engaging retainer. Retainer component 76 may be fashioned of a suitable polymeric material. For example, a polyphenylsulfone marketed under the trade designation "RADEL" by the American Oil Company, Inc., of Marietta, Ohio. Forward portion 78 of the retainer component 76 is attached to the collimator 72 utilizing a medical grade high temperature resistant epoxy adhesive. The collimator 70 is readily inserted upon the probe component 64, as well as removed therefrom for cleaning and sterilization. In this regard, the assembly is seen to be formed having smooth contours both externally and internally and is sterilizable using heat sterilization procedures.

Figure 3:
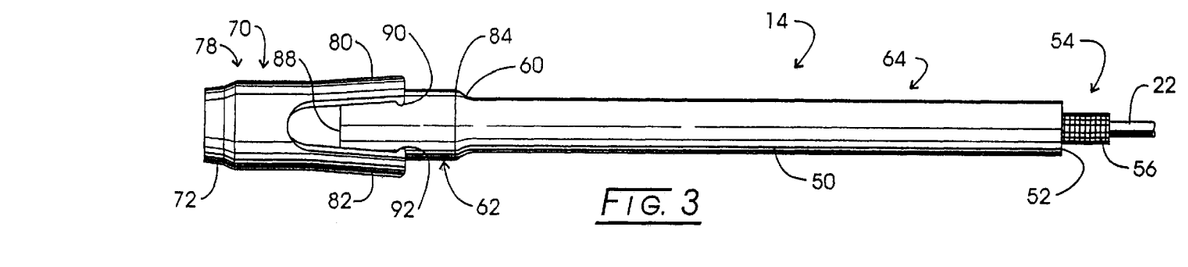
FIG. 3 is a side view of the assembly of FIG. 2 showing the collimator assembly in the process of being inserted upon the probe component.
Figure 4:
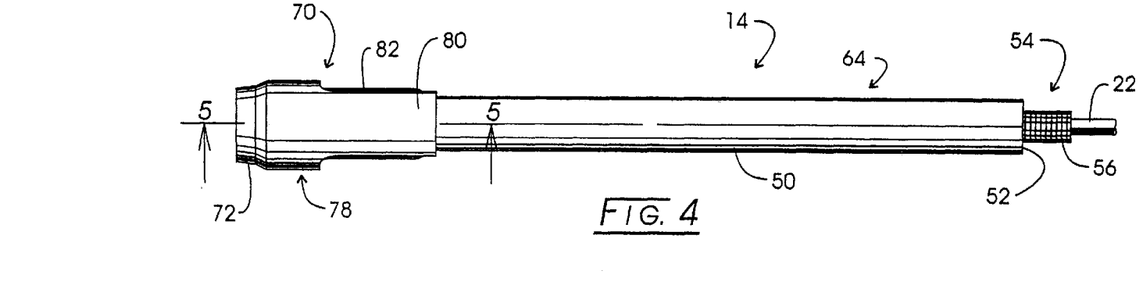
FIG. 4 is a side view of the probe apparatus of the invention showing the collimator assembly fully mounted upon the probe component.

Looking additionally to FIGS. 3 and 4, the procedure wherein collimator assembly 70 is installed upon the probe component 64 is illustrated. The dog components 90 and 92 are seen to have rounded rearward surfaces. The curvature 88 of the window assembly 62 functions to facilitate the forcing apart of leg portions 80 and 82 of the collimator 70 at the commencement of its insertion. However, that curvature 88 will be seen to have another important radiation blocking function. FIG. 3 shows that the resilient legs 80 and 82 are expanded apart as the dog components 90 and 92 are slid over the window assembly 62. Note that the transition region 60 is formed as a curved ramp which will cooperate with the forward surfaces of dogs 90 and 92. Accordingly, as seen in FIG. 4, upon full insertion and the seating of the collimator component 72 against window 86, the engagement of the forward surfaces of dogs 90 and 92 with the transition region curved ramp 60 provides for a rearward biasing of the entire collimator assembly 70 against the window 86 and its curvature at 88.

The probe 64 of the probe assembly 14 is structured such that the cadmium-telluride crystal which it supports is very rigidly retained against movement. This is in avoidance of noise which may be generated, for example, due to the piezoelectric characteristics of these critical detectors. Additionally, the structure is fashioned such that electrical noise is avoided. Such noise, for example, may be generated by the creation of a capacitance variation by relative movement between bias voltage carrying electrical components with respect to adjacent grounded components. Grounding of the components is important for the purpose of electrical shielding. Electrical noise avoidance also is enhanced by the mounting of the most sensitive components, i.e., an introductory integrator stage of the preamplification circuitry mounted within the handle component 50. These forward components are positioned very close to the bias carrying signal output developed from the cadmium-telluride crystal. Probe component 64 additionally is configured so as to be readily manufactured and to provide highly enhanced and desirable shielding in and of itself with respect to radiation phenomena directed transversely to the forward looking window 86.

Figures 5, 6:
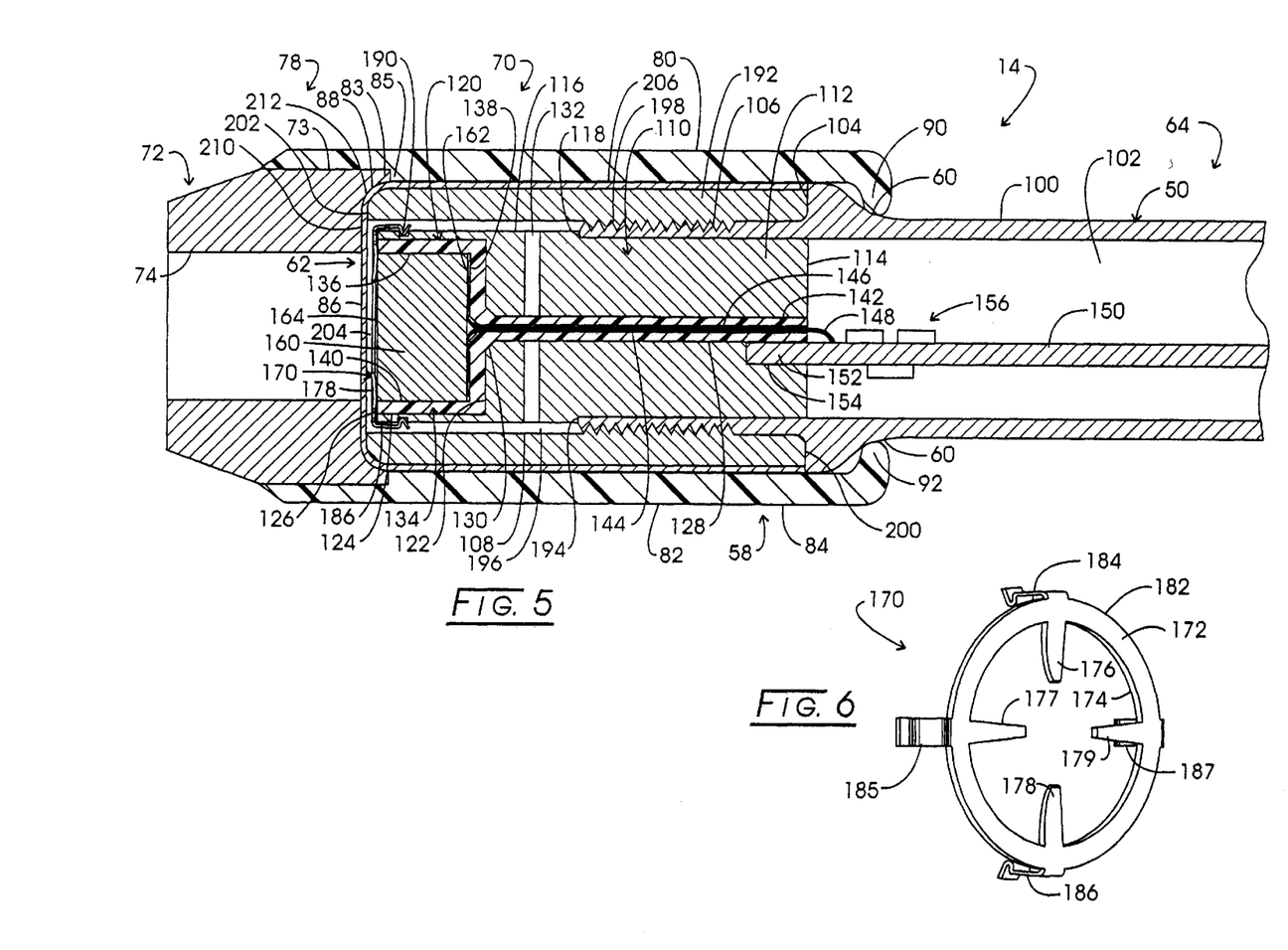
FIG. 5 is a partial sectional view taken through the plane 5—5 shown in FIG. 4.
FIG. 6 is a perspective view of a retainer and grounding assembly employed with the probe component of the invention.

Looking to FIG. 5, the handle component 50 is seen to be formed as a stainless steel cylindrical wall 100 which surmounts an internal handle cavity 102. At the forward region 58 of the handle 50, the noted curved ramp transition region 60 is developed. On the forward side of the transition region 60 there is formed a flat annular shoulder surface 104. Extending still forwardly, is a cylindrical connection region 106 fashioned of external threads. The forward portion 58 terminates at a forward annular surface or edge 108. Positioned within the handle cavity 102 at the forward region 58 is a crystal mount shown generally at 110. Mount 110 is formed of a material attenuating radiation, for example, a gold plated brass material or lead. The device 110 includes a mount rear portion 112 the cylindrical outer surface of which is adhesively attached to the cylindrical inner surface of wall 100. This rearward portion 112 extends to a rear surface 114 immediately adjacent the shoulder surface 104 of the transition region 60. Mount 110 extends forwardly from the forward region 58 of handle component 50, having a cylindrical mount outer surface 116 slightly greater diameter than the corresponding diameter at the rear portion 112 to provide a positioning edge 118 which abuts against the forward annular surface 108 of handle component 50. Outer surface 116 surmounts a forwardly opening mount cavity represented generally at 120 which has a circular bottom surface 122 and interior side surface 124 extending to an annular mount cavity edge or surface 126. Extending through the center of the cylindrical system mount 110 is a cylindrical channel 128 extending from a chamfered opening 130 at bottom surface 122 and through the rear surface 114. A cylindrical pressure relief and fixturing or mounting channel 132 is seen to extend through the center of the mount 110. Tightly fixed within the mount cavity 120 is a rigid, polymeric, electrically insulative crystal receiver represented generally at 134. Receiver 134 is formed having a forwardly opening crystal receiving cavity represented generally at 136. The cavity 136 is configured having an interior bottom surface 138 and interior sidewall surface 140. Note that the sidewall 140 extends to the mount cavity edge 126. Integrally formed with the crystal receiving cavity 136 is an elongate stem which extends from closely fitting or nesting relationship within the channel 128 of crystal mount 110 essentially from the chamfer 122 to the rear surface 114. The crystal receiver 134 may, for example, be formed of polytrafluoroethylene and may be ridgidly secured within crystal mount 110 utilizing a high temperature resistant epoxy adhesive. Note that the stem 142 incorporates a passageway 144 which retains a multi-strand electrical lead, the strands which are spread apart at the interior bottom surface 138 and are retained in abutment at that position without resort to adhesives or the like. The lead 146 is securely retained against any movement by the stem 142 and is seen at 148 to be curved and then attached by soldering to a bias conducting pad (not shown) mounted upon a printed circuit board 150. The forward portion 152 of circuit board 150 is seen to be rigidly mounted within a slot 154 extending inwardly from the rear surface 114 of crystal mount 110. Circuit board 150 additionally carries electrical ground (not shown) which is soldered at two locations (not shown) to rear surface 114. This provides for the conveyance of this specific ground to the crystal mount 110 as well as all components mechanically coupled with it including handle component 50. Circuit board 150 additionally includes the components forming a preamplification function. In particular, the initial stage of the preamplifier is an integrator stage having a high level of electronic sensitivity. The components of this stage are mounted in close proximity to the mounting of the circuit board 150 within the slot 154. Thus, essentially no physical movement of them occurs. Such components are represented generally at 156. Note, additionally, that they are shielded electrostatically by the grounded handle wall 100 and are located essentially at a thicker region of the handle, i.e., the transition region 60. The rigid mounting of these components which are associated electrically with lead 146 avoids the development of electrical noise phenomenon occasioned by a variable capacitance phenomenon caused by the movement of such components with respect to adjacently grounded structures.

Rigidly fixed within the crystal receiving cavity 136 is a cadmium-telluride crystal detector 160. This fixed and rigid mounting is accomplished without the intervention of adhesives or the like. Crystal 160 is retained compressively and the rearward face thereof is in freely abutting compressive engagement with the splayed strands of electrical lead 146 which are spread upon the interior bottom surface 138 of the cavity 136. Thus, the rearward face 162 of semiconductor crystal 160 receives a positive bias voltage. Correspondingly, it is necessary that electrical ground be applied to the forward face 164 of the crystal 160. For the instant utilization in conjunction with $^{99m}$Tc, the thickness of the semiconductor crystal 160 is selected as 4 mm. Its diametric extent is selected as 7 mm. The smaller diameter facilitates the utility of the apparatus 14 in being moved through an incision toward a sentinel node. As noted above, for the higher gamma energy radionuclide involved, the crystal 160 is operated in a trapping dependent mode wherein essentially all carriers resulting from photon events are trapped. By contrast, the cadmium-telluride crystal detector employed with the RIGS system performs in a different mode, having a thickness of 2 mm. Because of the low energy and small amount of radiation involved with that system, the diameter of the crystal is for example, 9 mm. Semiconductor crystal 160 is retained in the noted compressive attitude, intra alia, by a retainer and grounding assembly represented generally at 170. Looking to FIG. 6, the assembly 170 is seen to be formed of an electrically conductive flat metal ring 172 which is dimensioned to be positioned over the annular cavity edge 126 as seen in FIG. 5. Thus, its inner edge 174 will not block the forward face 164 of cadmium-telluride crystal 160. Integrally formed with the ring 172 and extending inwardly from the edge 174 are four ground conveying tines 176–179. Tines 176–179 are bent in a rearward sense so as to contact the forward face 164 of semiconductor crystal 160, applying both pressure and electrical ground thereto. Additionally integrally formed with the ring 172 and extending perpendicularly from its outer edge are four resilient dogs 184–187. Looking additionally to FIG. 5, it may be observed that assembly 170 is mounted upon crystal mount 110 by engagement of the dogs 184–187 within an annular groove 190 formed within the forward outer surface 116 of crystal mount 110. Assembly 170 is formed of a resilient, spring-type metal, for example containing beryllium and copper, and may be plated with a metal such as gold. Because the forward face of cadmium-telluride crystal 160 typically is coated with a very thin layer of gold, the resulting gold on gold contact with assembly 170 reduces triboelectric noise phenomena caused by the contact of dissimilar materials. Ground is conveyed from the dogs 184–187 to the ring 172 and tines 176–179. In fabricating the probe 64, a subassembly initially is made of the components including the crystal mount 110, crystal receiver 134, crystal 160, lead 146, circuit board 150, crystal 160 and the retainer grounding assembly 170. That subassembly then is mounted within the cavity 102 of handle component 50. A heat resistant electrically conductive epoxy adhesive is used for connecting the mount rear portion 112 with the cavity 102 at forward region 58.

An alternative for the retainer and grounding assembly 170 which has been successfully employed with the probe 64 employs a stretched nylon web which is secured to the crystal mount 110 through the utilization of a groove and o-ring arrangement. Ground is applied to the forward face 164 of the crystal 160 by very thin platinum wires embedded within the crystal mount 110 and extended over the front face 164. These wires are retained in position by virtue of their being underneath the noted nylon web. Such a mounting is described in U.S. Pat. No. 5,070,878 by Denen, entitled "Detector And Localizer For Low Energy Radiation Emissions," issued Dec. 10, 1991 and assigned in common herewith. The drawback of that arrangement, however, is that the nylon material is not autoclavable and resort must be made to get lengthy gas-based sterilization procedures.

Surmounting the subassembly as above described is the cup-shaped window assembly 62. Assembly 62 is comprised of a sleeve shield 192 formed of material attenuating radiation, such as tungsten, having an open cylindrical interior surface 194 of diametric extent greater than cylindrical outer surface 116 of crystal mount 110. Thus, a cylindrical gap 196 is present intermediate the interior surface 194 and the mount surface 116. Below the gap 196 is a shield connection region 198 which provides threaded connection with the externally threaded region 106 formed within the handle component 50 at its forward region 58. The sleeve shield 192 extends from its annular rear edge 200 abuttably engaging the shoulder surface 112 to a rounded annular forward edge 202. Note that the edge 202 extends forwardly from the corresponding mount cavity edge 126 a distance defining a forward gap 204 between the thin aluminum window 86 and the forward face 164 of cadmium-telluride crystal 160. This gap 204 serves as an acoustic filter to aid in the avoidance of noise generation due to the piezoelectric characteristics of such cadmium-telluride crystals. In general, the gap will have a width of about 0.015 inch. Window 86 is seen to extend about the curvature 88 to provide a cylindrical sidewall 206 which is coextensive with the outer surface of cylindrical sleeve shield 192. Attachment with the sleeve shield 192 is provided utilizing a surgical-grade electrically conductive epoxy adhesive. Such adhesive generally will contain an amount of silver to provide the noted conductivity. Alternately, the cup-shaped aluminum component can be coupled to the sleeve shield 192 by swaging procedures or the like. The sleeve shield 192 component of the assembly 62 provides highly desirable additional shielding of the crystal detector 160 from side attacking radiation. In addition to structurally supporting the thin window region at 86, the sleeve shield forward edge region beneath curvature 88 also contributes to the collimation function of tungsten collimator 72. In this regard, FIG. 5 reveals that the rearward end surface 210 of collimator 72 is concavely configured at the region of its periphery 212 in compliment with the curvature 88 of the window 86 and the underlying tungsten forward edge 202 of the sleeve shield 192. Thus, the curved forward edge 202 and the curved concaved region 212 overlap to block side attaching radiation which otherwise could migrate through the transmissive aluminum material of the window components 86 and 206. The gap defining extension of the sleeve shield 192 at its forward edge 202 serves the function of providing physical support to the thin and somewhat delicate aluminum window component and provides important shielding for the crystal. Because the sleeve shield 192 is intimately engaged with the handle component 50, it also is electrically grounded and that ground additionally is applied to the aluminum window 86. No variable capacitance induced electrical noise can be generated with this rigid structuring. The cup-shaped window assembly 62, by virtue of the sleeve shield arrangement provides a structurally reinforced assembly at curvature 88 which pen-its a positioning of the collimator assembly 70 upon the probe component 64, as described above in conjunction with FIGS. 3 and 4, without causing damage to the relatively weaker components.

The structuring of the sleeve shield components and associated aluminum window components to form the assembly 62 also aids in the manufacturer of the probe 64. Following the formation of the above noted subassembly, the cup-shaped window assembly 62 simply is screwed on to the forward region 58 of the handle component 50. FIG. 5 also reveals that when the collimator assembly 70 is installed upon the probe component 64, the dog components 90 and 92, by virtue of their engagement with the ramp defining transition region 60 of handle component 50 will be biased rearwardly to assure continued closely abutting engagement of the collimator rearward end surface with the curvature 88 of the window 86. It may be further noted that the diameter of the interior surface 74 of the collimator 70 corresponds with the diametric extent of the forward surface 164 of crystal detector 160. Generally, the lengthwise extent of the interior surface 74 will fall within a range of lengths corresponding with the diameter of crystal 162 to a value of twice that diameter. As shown at 73, the diameter of the exterior surface of collimator 72 may be larger than that of window assembly 62, thus forming an annular collimator shoulder 83 which abuts retainer shoulder 85 formed within retainer component 76. No fixture then is required to properly position and adhesively attach the collimator 72 with the retainer component 76.

Figure 7:
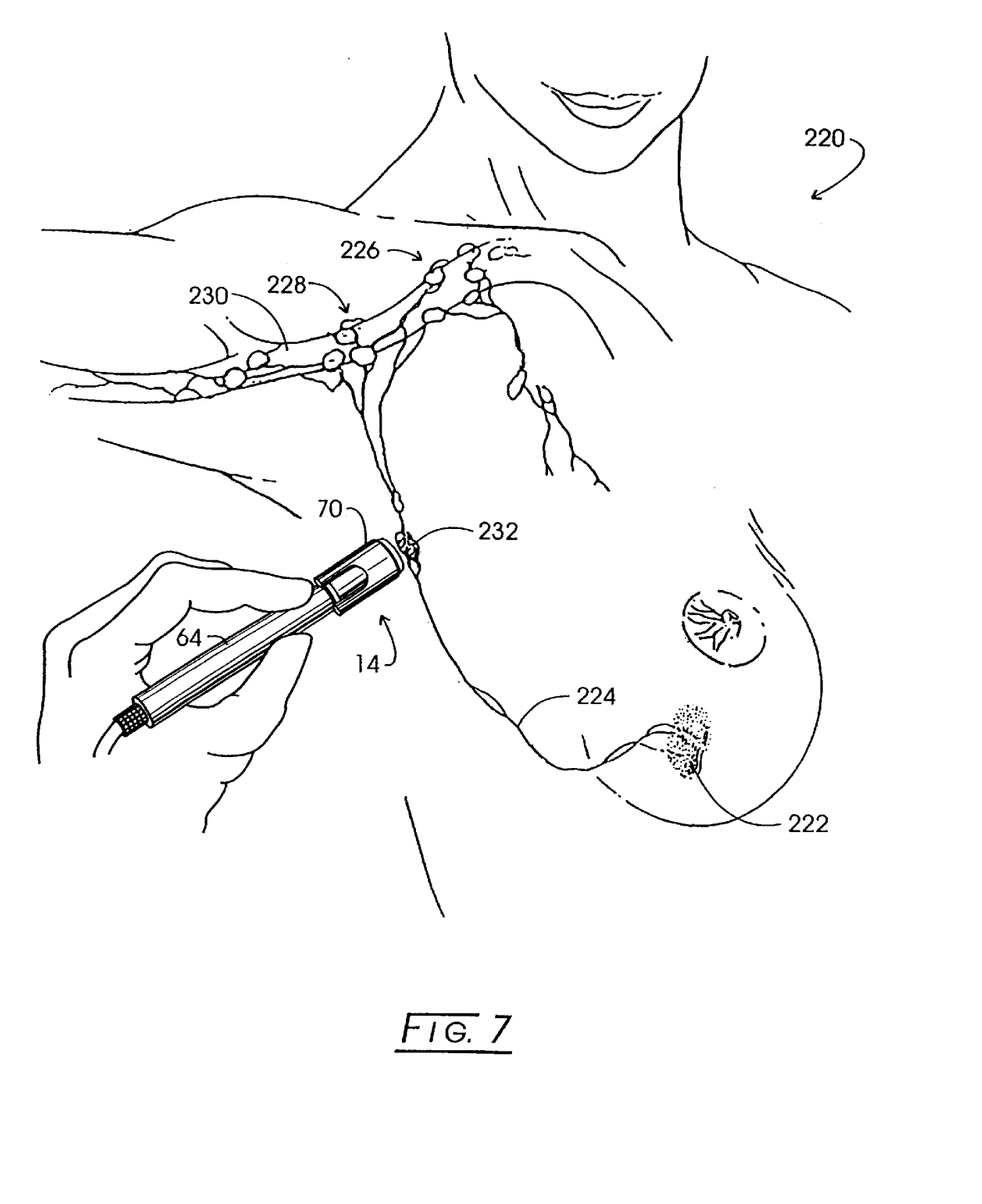
FIG. 7 shows a view of the upper torso from an interior aspect illustrating lymph duct drainage from a breast tumor.

A relatively close proximity of a sentinel node to the site of a lesion occurs quite often in connection with the identification of sentinel nodes in the course of the surgical treatment of breast cancer. Looking to FIG. 7, an illustration of the breast region is represented in general at 220. At this breast region 220 there is depicted an internally disposed tumor 222. By injecting a radiopharmaceutical in the vicinity of the tumor 222, a procedure may be carried out to locate a sentinel node. Specifically, the practitioner will know that the lymph duct involved and leading to the sentinel node will be directed toward the axilla. Such a lymph duct is shown at 224. While the lymph duct may be tracked, typically the practitioner is aware that drainage of the radiopharmaceutical will be toward the lymph node basin at the axilla. In this regard, the infraclavicular nodes are shown in general at 226 and the lateral group at 228 in adjacency with the axillary vein 230. As the practitioner scans the axilla, a substantial increase in count rate activity will be encountered when the collimated window of the probe assembly 14 is over the sentinel node. A variable frequency sound will be heard by the practitioner, whereupon the threshold of probe aural response may be elevated utilizing knob 48 (FIG. 1) until the sound terminates. A small incision then is made and the tracking procedure proceeds utilizing the thresholding approach. Ultimately, the forward surface of the collimator 70 is in adjacency with the radiopharmaceutical collecting sentinel node 232. However, during this procedure, transverse radiation from the vicinity of the lesion 222 will impinge against the side surfaces of the probe assembly 14. Thus, an effective collimator as at 70 is called for as well as effective side shielding as provided by the sleeve shield 192.

Figure 8A:
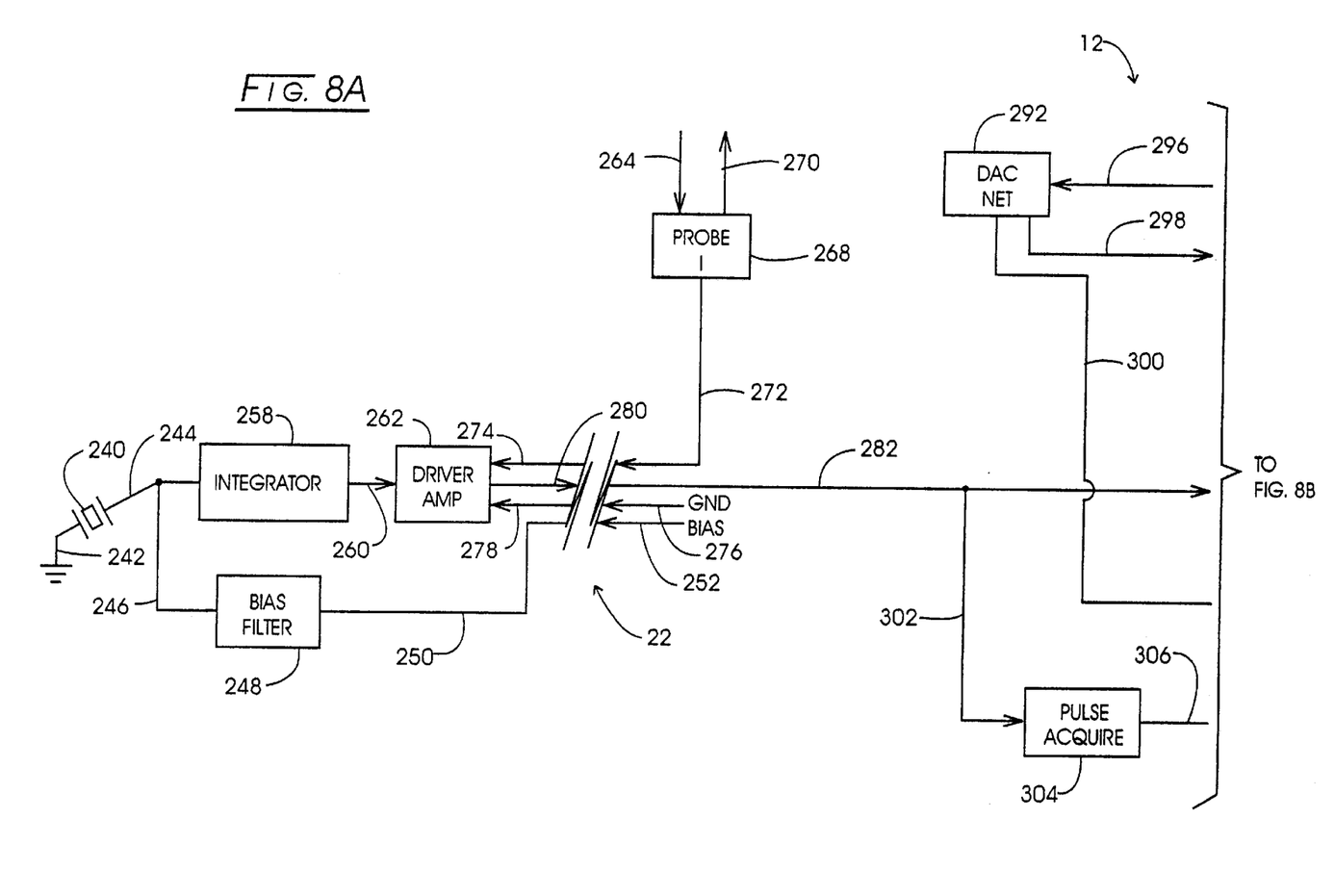
FIGS. 8A and 8B combine as labeled thereon to provide a block diagrammatic representation of the circuit employed with the control assembly and probe assembly shown in FIG. 1.
Figure 8B:
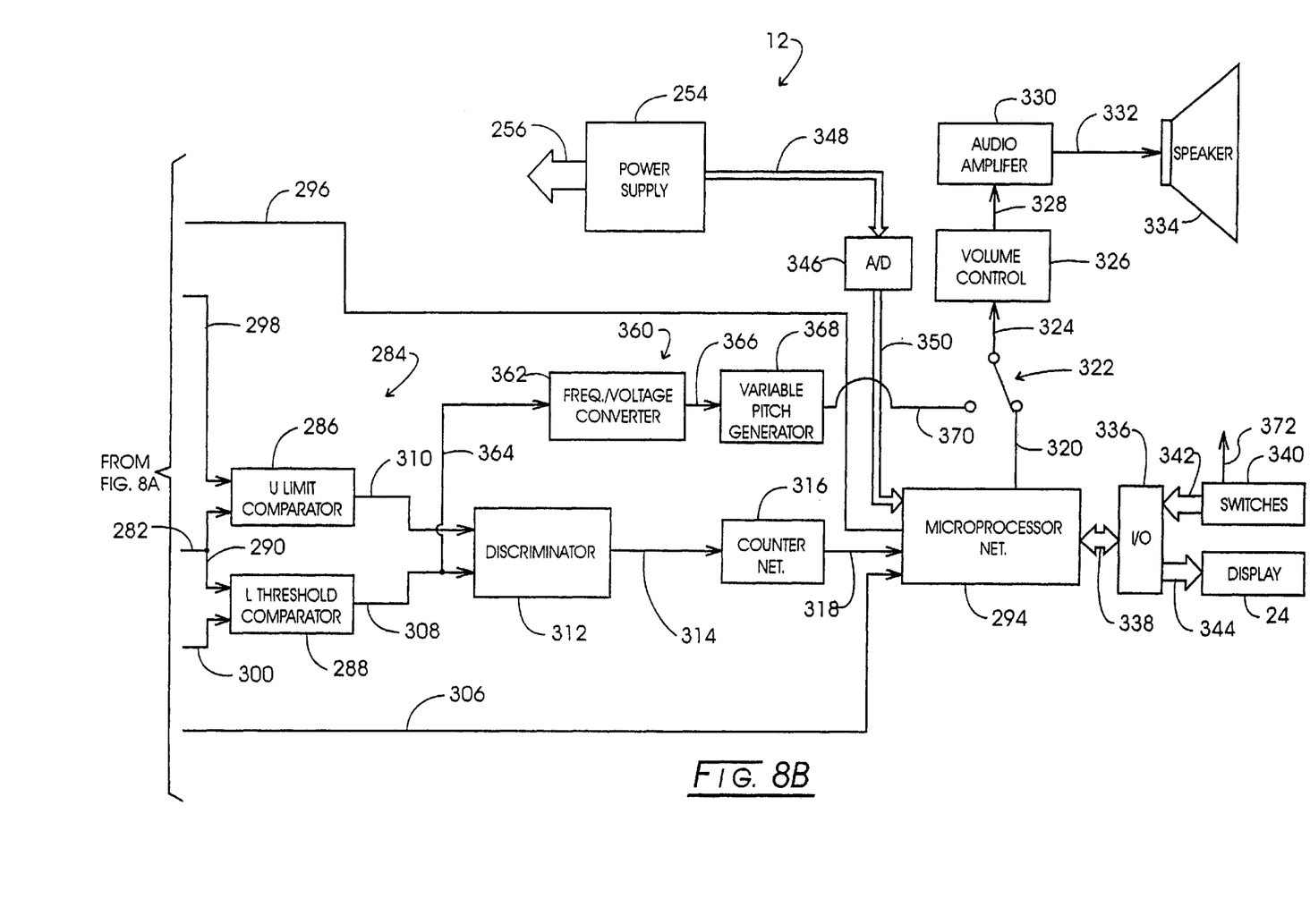

Referring to FIGS. 8A and 8B, a blocked diagrammatic representation of the circuitry employed with the system 10 is portrayed. These figures should be considered in mutual adjacency in the manner labeled thereon. In FIG. 8A, a crystal such as a cadmium-telluride crystal as at 160 is represented at 240. Crystal detector 240 is shown having one face coupled to ground through line 242, while the opposite, biased face thereof is coupled via lines 244 and 246 to a bias filter represented at block 248. The input to filter 248 is represented at line 250 as being applied through the cable as described earlier at 22, which number reappears in the instant figure. The bias input, as represented at line 252, emanates from a multi-output power supply shown in FIG. 8B at block 254. These various outputs are represented, in general, by an arrow 256 extending from block 254.

Returning to FIG. 8A, line 244 from the crystal detector 240, carrying a detector output corresponding with radiation emissions impinging upon the detector, is seen to extend to an integrator stage represented at block 258. This integrator stage 258 has been discussed in connection with the components 156 in FIG. 5. In this regard, they are mounted in a highly rigidified mechanical structural environment and within a grounded transition region 60 of enhanced stainless steel metal thickness. The integrator stage 258 thus forms part of the treatment circuit or preamplification function mounted upon circuit board 150. The integrated valuation of detected radiation emissions then is shown directed, as represented by line 260 to a driver amplification network shown at block 262. A preferred preamplification circuit comprised of blocks 258 and 262 is described in U.S. Pat. No. 5,441,050 by Thurston and Olson, issued Aug. 15, 1995, entitled: "Radiation Responsive Surgical Instrument," assigned in common herewith and incorporated herein by reference. A d.c. power supply is provided from the power supply represented at block 254 and arrow 256 (FIG. 8B) for the preamplification function. This power supply is directed, as represented at line 264, to a probe current network represented at block 268. Under microcomputer control, as represented at line 270, the network 268 develops signals, for example, determining whether the probe instrument 64 has been properly connected to the console 12. Delivery of the d.c. power supply for the preamplification function is represented at lines 272 and 274. Line 274 forms a component of flexible cable 22. Electrical ground is generated from the power supply described at block 254 and arrow 256 in FIG. 8B and is shown to be extended by a line 276 within the control assembly 12, as well as line 278 within the probe 64. The integrator 258, driver amplification stages 262 and bias filter 248 are components of a treatment circuit housed within the cavity 102 of the handle component 50. The preamplification function electrically treats the detector output of detector crystal 240 to, in turn, provide output signals corresponding therewith along line 280 of cable 22 for introduction to the control assembly 12, the corresponding signal carrying line of which is shown at line 282. Line 282 extends to the input of an energy window network represented in FIG. 8B in general at 284. Network 284 functions to evaluate the count output to derive a validated photon count signal. Looking to FIG. 8B it may be observed that the gamma energy window network 284 includes an upper limit comparator represented at block 286, as well as a lower threshold comparator represented at block 288. The count output or photon event signals at line 282 are submitted simultaneously to each of these comparator functions 286 and 288, as represented at line 290. Correspondingly, the comparison values or limits associated with the upper limit comparator 286 are applied from a digital-to-analog converter (DAC) seen in FIG. 8A at block 292. Converter 292 is under the control of a microprocessor network represented at block 294 (FIG. 8B), such digital control to device 292 being asserted at line 296. The upper limit value asserted at the comparator 286 is provided at line 298 from DAC 292. Correspondingly, the lower threshold value for comparator function 288 is asserted from DAC 292 via line 300. FIG. 8A also reveals that the signals at line 282 are directed, as represented at line 302, to a pulse acquire function represented at block 304. Network 304 functions, when activated by the microprocessor network 294, to acquire the value of the highest pulse amplitude witnessed at line 282. Periodically, this information then is transmitted to the microprocessor network 294 as represented by line 306. Representing a form of peak detector, the network 304 sometimes is referred to as a "snapshot circuit". With the arrangement shown, the probe assembly 14 derives count outputs in response to photon emissions which are confronted at the forward face of crystal detector as represented at 240. Those count outputs will have an amplitude corresponding to the energy of interest of the photon emissions. Additionally, the signals may represent spurious phenomena such as cosmic rays, Compton scattering, capacitance variance noise, piezoelectric effects and the like. Accordingly, the energies of the count outputs or amplitudes thereof are evaluated at the energy window network 284 as seen in FIG. 8B. In order for the network 284 to work effectively, it is important to have the signals representing energy of interest well spaced apart in terms of energy from the noted noise phenomena. Effective windowing has been found to be associated with the mode of operation of the compound crystal detector. That performance mode is selected with respect to the radionuclide energies involved, and for the present embodiment, the mode is a trapping-dependent operational mode.

Lower threshold comparator function 288 will promulgate a pulse at line 308 when the signal asserted thereat exhibits an amplitude of value equal to or above a threshold value established, as noted above, from line 300. Correspondingly, the count output signals from line 282 will be evaluated by the upper limit comparator function 286 such that when the count output signal exhibits an amplitude of value above the upper limit value established from line 298, a pulse will be promulgated at line 310. When the console 12 is employed with a RIGS mode of operation, the outputs from lines 308 and 310 then are directed to the input of an asynchronous, sequential, fundamental mode discriminator circuit represented at block 312. Circuits as at block 312, while being sequential in nature, are not synchronized in any way with a clock signal. Such circuits as at block 312 are described in U.S. Pat. No. 5,475,219 by Olson, entitled: "Validation Of Photon Emission-Based Signals Using An Energy Window Network in Conjunction With A Fundamental Mode Discriminator Circuit." The discriminator function represented at block 312 serves to generate photon event outputs for count associated signals in the form of finite pulses as at line 314. Such pulses occur with the presence of a count output signal at line 282 which represents a photon emission which is valid from the standpoint of the energy range of interest associated with it.

The pulsed signals at line 314 are provided to a counter network represented at block 316. These pulses at line 314 are counted by the network 316, whereupon, as represented at line 318, count data is submitted to the microprocessor network 294 for statistical analysis. A function of counter network 316 may be implemented in software as described in the above-referenced U.S. Pat. No. 4,889,991. Microprocessor network 294 performs under a variety of operational modes depending upon the user inputs to the function switches at array 28 (FIG. 1) as well as any calibration activity undertaken by the user. In general, it functions to provide outputs to two output components, one aural type generated from a speaker, and the other a visual output at display 44. Generally, a "siren" type of signal manifested with a predetermined frequency variation is asserted, as represented by line 320, through a mode switch 322 and line 324 to a volume control function represented at block 326. A volume adjustment having been carried out at the control 326, the volume adjusted signal is directed, as represented at line 328 to an audio amplification circuit represented at block 330. The circuit at block 330, in turn, as represented at line 332, drives a speaker 334. With the noted "siren" arrangement, the frequency output from speaker 334 increases with an exponential change from 20 Hz to 1200 Hz when the average count rate determined by the system 10 exceeds a preset threshold level which is statistically significant over background count rates. The "siren" mode is accessed by the user from console 12 by sequentially actuating switch 36 then switch 34. This "siren" mode of performance is described in detail in the above-referenced U.S. Pat. No. 4,889,991 by Ramsey and Thurston.

Microprocessor network 294 performs in conventional fashion with an input/output network as represented at block 336 and dual directional arrow 338. This input/output port function 338 provides for appropriate scanning of pertinent console 12 mounted switches, as represented at block 340 and arrow 342. The output port also drives the display 24, again represented by the same numeration in block form as represented by arrow 344. Further, the microprocessor network 294 may be employed to monitor the performance of the power supply represented at block 254. This is shown being carried out by the interaction of microprocessor network 294 with an analog-to-digital converter represented at block 346 and having an association represented by arrows 348 and 350. The converter 346 functions to digitize analog values at the power supply 254 for submittal to microprocessor network 294.

Components of the adjunct circuitry of system 10 are represented in general at 360. This adjunct system performs in conjunction with higher energy level radionuclides and the probe apparatus 14. The components of system 360 include a frequency-to-voltage converter represented at block 362 which responds to the count associated signals from the lower threshold comparator at block 288, as represented at lines 308 and 364, to provide a rate output level signal at line 366 corresponding with the frequency of those count associated signals. This signal will be provided as a d.c. voltage level which extends within a dynamic range of, for example, 0 to 2.5 volts. That signal then is directed to a variable pitch generator function represented at block 368. The generator at block 368 serves to provide the noted initial ranging feature and a count rate thresholding feature which may be controlled from knob 48 or the up/down switches 49 and 50 (FIG. 1). Additionally included in the function at block 368 is a post-thresholding amplification network having a gain corresponding with the threshold level value to permit full scale performance of the speaker 334 and linear LED array 44 (FIG. 1). The output of the generator function 368 is shown at line 370 extending to one terminal of switch 322. Microprocessor network 294 continues to provide volume control during the operation of the generator function 368 in response to the actuation of switch 38 (FIG. 1). An output represented at arrow 372 extends to a "beep" generator function which provides a auxiliary audible switch feedback for the user.

Figure 9:
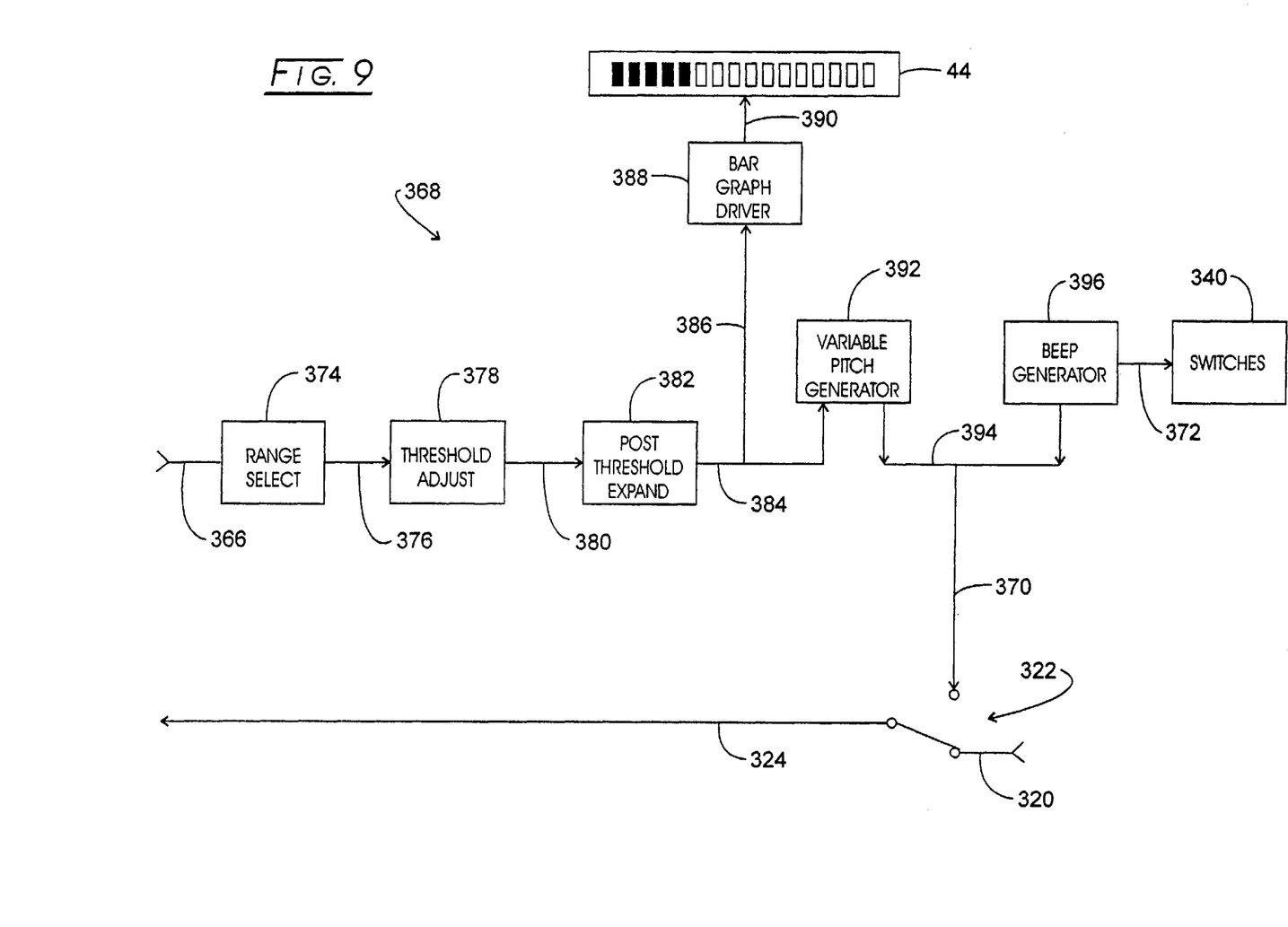
FIG. 9 is a block diagram showing variable pitch generator components of the system of the invention.

Referring to FIG. 9, a block diagrammatic representation of the generator function 368 is provided. The figure reveals that the output from the converter network 362 at line 366 is directed to a range select function represented at block 374. Function 374 provides for the earlier-described selection of ranges of counts per second such that an initial approach is taken to derive full scale drives for the visual and aural cueing components, i.e., LED array 44 and speaker 334. Upon selecting an appropriate range, the range adjusted signal level is directed, as represented at line 376 and block 378 whereat a threshold is established with respect to the incoming signal at line 376. That threshold represents a percentage of full scale dynamic range of the signal. Additionally, minimum and maximum values to which a threshold percentage can be set are developed. Without more, where high thresholds are employed, the signal or level available for developing a drive for the LED array 44 or speaker 334 would be inadequate. A minimum threshold level maybe imposed to avoid sound outputs resulting from environmental noise. The adjusted count rate signal at line 380 is directed to a post threshold amplification network represented at block 382. Network 382 is configured having a gain which corresponds with the threshold level value set at function 378 such that it carries out an amplification of the adjusted count rate signal at line 380 to provide an amplified count rate signal at line 384. That amplified signal lies at levels within a predetermined output dynamic range. The dynamic range is established by the aural cueing and drive demands of the LED array or bar graph 44. In this regard, line 384 is tapped at line 386 and the signal thereat is directed to a bar graph driver function represented at block 388. Driver 388 then drives the array 44 as represented at line 390. Line 384 also is seen directed to a variable pitch generator represented at block 392 which functions to produce a drive signal at line 394 which is directed to line 370. The signal line 370 then will produce a speaker drive output at a pitch corresponding with the drive signal asserted thereat and which lies between a zero pitch level and a maximum pitch level which corresponds with the noted dynamic range that is maintained. Driven aural feedback from operation of switches 340 because, for the present embodiment, the microprocessor driven aural feedback from operation of switches 340 is not present, an additional "beep" generator is provided as represented at block 396. Generator 396 functions to generate a "beep" via lines 394 and 370 at such time as any one of the switches 308 are actuated by the operator. Line 370 is reproduced from FIG. 8B, as well as the designations for switch 322, line 320 and line 324.

Figure 10:
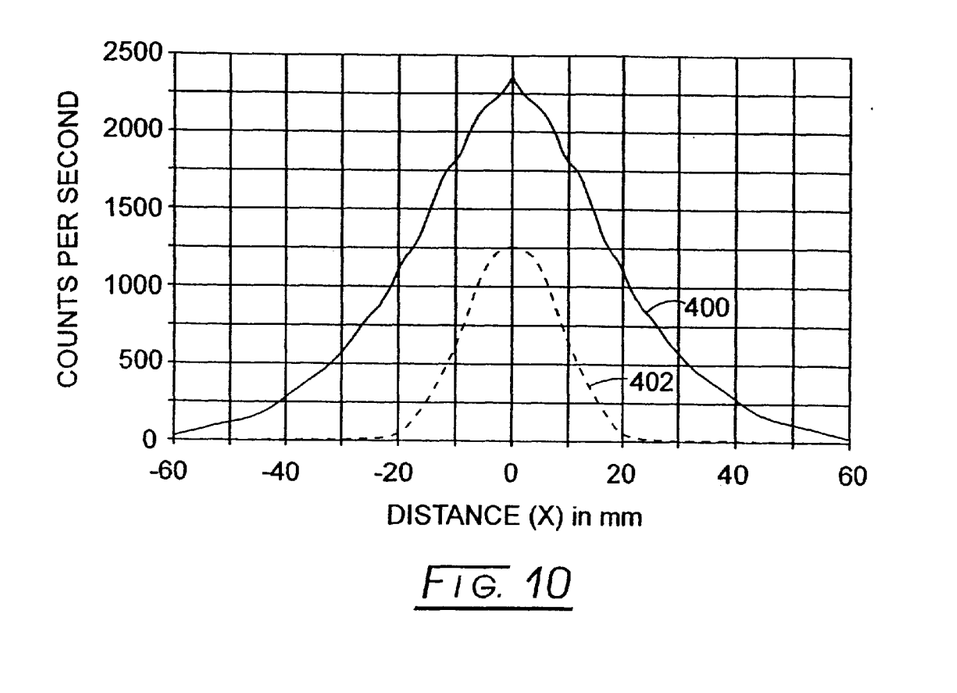
FIG. 10 is a plot combination of count rate versus lateral distance from a check source representing the operation of the probe assembly of the invention.
Figure 11:
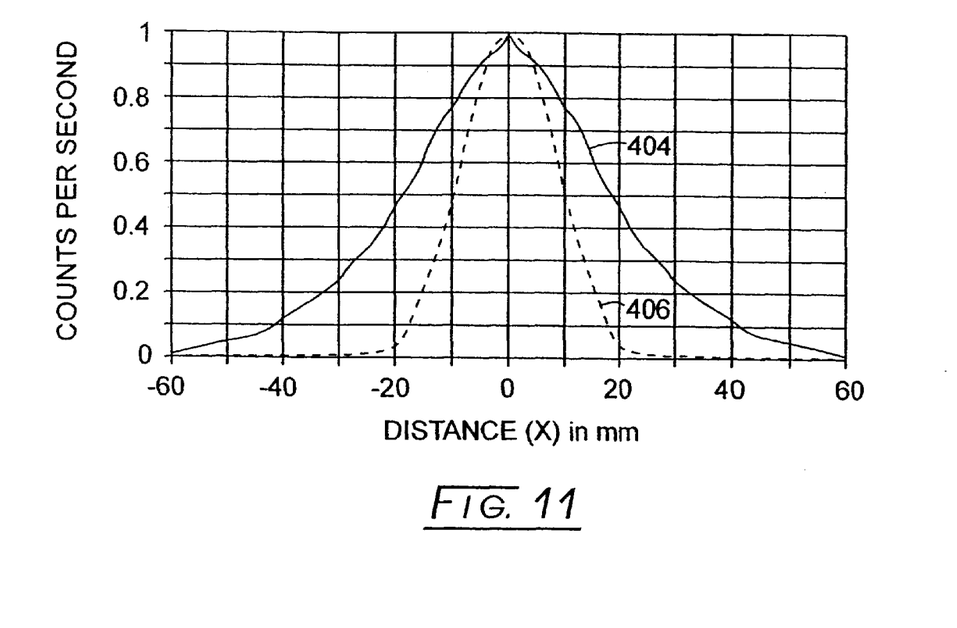
FIG. 11 is a normalized plot of the curve combination shown in FIG. 10.

Tests have been carried out with the probe 64 and with the probe assembly 14 incorporating a mounted collimator assembly 70. In this regard, a check source, $^{99m}$Tc was employed at a fixed distance from the forward face of the probe window 86. The source then was moved transversely to the center line of the cylindrical probe by predetermined distances and the count rate resulting therefrom was plotted with respect to distance. Looking to FIG. 10, curve 400 shows the performance of the probe 64 without collimation, while, correspondingly, curve 402 represents the output of the probe assembly 14 with the collimator 70 attached. Note that the count rate performance amplitude is attenuated when the collimator 70 is attached. However, the positional accuracy remains. The latter result is demonstrated in the curves of FIG. 11. In that figure, curve 404 is a normalized representation of curve 400 of FIG. 10. In this regard, the amplitude values represented at curve 400 were divided by the maximum amplitude value or photopeak. Correspondingly, curve 406 represents a similar normalization of curve 402.

Since certain changes may be made to the above described system and apparatus without departing from the scope of the invention herein involved, it is intended that all matter contained in the description thereof and shown in the accompanying drawings shall be interpreted as illustrative and not in a limiting sense.

What is claimed is:

1. Probe apparatus for detecting and locating sources of radiation emission, comprising:

a handle component extending from a rearward end to a forward region with a forwardly facing tip, having a wall surmounting an interior handle cavity, said wall having an outwardly extending transition portion at said forward region and having a handle connection region located forwardly from said transition portion;

a crystal mount, formed of material attenuating said radiation, having a mount rear portion with a rear surface mounted within said handle cavity and extending forwardly from said forward region tip with a cylindrical outer mount surface of first diametric extent to a forwardly opening mount cavity with an interior bottom surface and interior side surface extending forwardly to a mount cavity edge, said mount having a channel extending from said interior bottom surface to said rear surface;

a rigid, polymeric electrically insulative crystal receiver mounted within said mount cavity and having a forwardly opening crystal receiving cavity with an interior bottom surface and an interior sidewall surface extending toward said mount cavity edge;

a bias conveying and signal receiving lead assembly extending from said crystal receiving cavity interior bottom surface through said channel and into said handle cavity;

a crystal detector mounted in closely nesting relationship within said crystal receiving cavity, having a rearward face in abutting bias conveying engagement with said lead assembly at said receiving cavity interior bottom surface, said crystal detector extending to a forward face of predetermined diameter adjacent said mount cavity edge and being responsive to radiation impinging upon said forward face to provide a detector output;

a cup-shaped window assembly including a sleeve shield formed of material attenuating said radiation, having an open cylindrical interior surface, having a forward portion of second diametric extent greater than said first diametric extent, a shield connection region located rearwardly therefrom and removably connected with said handle component handle connection region and a length extending between a rear edge and a forward edge, said rear edge being adjacent said transition region and said forward edge extending a gap defining distance forwardly from said mount cavity edge when said shield connection region is connected with said handle connection region, and a window formed of radiation transmissive material extending over said sleeve shield at said forward edge in spaced relationship from said crystal detector to define a gap;

a treatment circuit located within said handle cavity for applying said bias to said crystal detector rearward face through said lead assembly and applying electrical ground to said crystal mount, and responsive to said detector output to provide output signals corresponding therewith; and a retainer and grounding assembly mounted upon said crystal mount and over said mount cavity edge, abuttably and compressibly retaining said crystal detector against said lead assembly at said receiving cavity bottom surface and abuttably conveying electrical ground from said crystal mount to said crystal detector forward face.

2. The probe apparatus of claim 1 including a collimator assembly comprising:

a collimator having a wall of thickness and material attenuating said radiation, having an open cylindrical interior surface of diameter corresponding with said predetermined diameter of said crystal detector at said forward face, having an exterior side surface and a rearward end surface, said rearward end surface being positionable in abutting adjacency with said window; and a polymeric retainer component having a forward portion fixed to said collimator exterior side surface and having two, integrally formed resilient rearwardly disposed leg portions extending to inwardly depending dogs removably engageable with said handle component transition portion when said collimator rearward end surface is in abutting adjacency with said window.

3. The probe apparatus of claim 2 in which:

said collimator is formed having an exterior wall with an outwardly extending collimator shoulder with an annular surface; and said polymeric retainer component is formed having a retainer shoulder which is configured for abuttable contact with said collimator shoulder surface.

4. The probe apparatus of claim 2 in which:

the outer periphery of said window and said sleeve shield forward edge are mutually configured having a predetermined curvature; and said collimator rearward end surface is concavely configured at the periphery thereof in compliment with said predetermined curvature to extend in nesting relationship over said window and said shield forward edge.

5. The probe apparatus of claim 1 in which:

said handle component wall is cylindrical, said transition portion extends to a forwardly disposed shoulder surface; and the said sleeve shield rear edge is positioned in abutting engagement with said shoulder surface.

6. The probe apparatus of claim 1 in which;

said handle component wall is cylindrical and said transition portion is configured as an annular upperwardly and forwardly sloping ramp;

including a collimator assembly, comprising:

a right cylindrical collimator having a wall of thickness and material attenuating said radiation, having a cylindrical interior surface of diameter corresponding with said predetermined diameter of said crystal detector forward face;

having exterior side surfaces and a rearward end surface, said rearward end surface being positionable in abutting adjacency with said window; and a polymeric retainer component having a cylindrically shaped forward portion fixed to said collimator exterior side surface and having two, integrally formed resilient rearwardly disposed leg portions extending to inwardly depending dogs removably and compressibly abuttable with said handle component transition portion to effect application of a rearwardly directed bias of said collimator rearward end surface against said window.

7. The probe apparatus of claim 1 in which:

said crystal mount is formed having a retainer groove spaced a predetermined distance inwardly from said mount cavity edge; and said retainer and grounding assembly includes an electrically conductive annular ring positioned upon said crystal mount as said mount cavity edge, compressibly retained thereon from said retainer groove and including at least one resilient ground conveying tine in compressive abutting engagement with said crystal detector forward face.

8. The probe apparatus of claim 1 in which:

said crystal mount is formed having a retainer groove spaced a predetermined distance inwardly from said forward cavity edge; and said retainer and grounding assembly includes a flat ring formed of resilient metal positioned upon and coextensive with said mount cavity edge and compressibly retained thereon from said retainer groove, said ring including a plurality of inwardly depending ground conveying tines in compressive abutting engagement with said crystal detector forward face.

9. The probe apparatus of claim 8 in which:

said annular ring includes at least two resilient integrally formed dogs depending therefrom and in engagement with said retainer groove for compressibly retaining said annular ring upon said crystal mount and conveying said ground.

10. The probe apparatus of claim 9 in which:

said forward face of said crystal detector is configured with a surface coating of a given metal; and said retainer and grounding assembly is configured with a surface coating of said given metal.

11. The probe apparatus of claim 1 in which:

said rigid polymeric crystal receiver includes an elongate integrally formed stem positioned within and extending through said mount channel; and said lead assembly extends through and is retained within said stem.

12. The probe apparatus of claim 1 in which:

said treatment circuit includes an integrator stage having components mounted upon a circuit board; and said circuit board is fixed to said crystal mount rearward portion, said components being located in close adjacency with said rearward portion and said mount channel.

13. The surgical system of claim 12 in which said circuit board extends rearwardly outwardly from a rigid mounting with said crystal mount rearward portion within said interior handle cavity.

14. The probe apparatus of claim 1 in which said electrically insulative crystal receiver interior sidewall surface is configured to abuttably engage the said side surface of said crystal detector.

15. Probe apparatus for detecting and locating sources of radiation emission, comprising:

a probe component, including:

a handle component extending from a rearward end to a forward region, having a wall defining an interior handle cavity, said wall having an outwardly extending transition portion at said forward region configured as a ramp;

a crystal mounting assembly supported from said forward region;

a cylindrical crystal detector supported by said crystal mounting assembly, having a rearward face and extending to a forward face having a predetermined diameter;

a circuit assembly for deriving detector outputs from said crystal detector and having a treatment network within said handle cavity deriving output signals corresponding with said detector outputs; and a forward assembly mounted upon said handle component forward region and extending from said transition portion to a radiation transmissive window adjacent said crystal detector forward face; and a collimator assembly, including:

a collimator having a wall of thickness and material attenuating said radiation, having an open, cylindrical interior surface of diameter corresponding with said forward face predetermined diameter, having an exterior side surface and a rearward end surface, said rearward end surface being positionable in abutting adjacency with said window; and a polymeric retainer component having a forward portion fixed to said collimator exterior side surface and having two, integrally formed resilient rearwardly disposed leg portions extending to inwardly depending dogs removably engagable with said handle component transition portion when said collimator rearward end surface is in said abutting adjacency with said window.

16. The probe apparatus of claim 15 in which:

said handle component wall is cylindrical, said transition portion extends to a forwardly disposed shoulder;

said forward assembly includes a cylindrical sleeve shield formed of material attenuating said radiation, having an open cylindrical interior surface positioned around said crystal mounting assembly, having a length extending between a rear edge and a forward edge, said rear edge being in abutting engagement with said shoulder and said forward edge extending a gap defining distance forwardly from said crystal detector forward surface; and said forward edge supporting said window in spaced relationship from said crystal detector forward face.

17. The probe apparatus of claim 16 in which:

the outer periphery of said window and said sleeve shield forward edge are mutually configured having a predetermined curvature; and said collimator rearward end surface is concavely configured at the periphery thereof in compliment with said predetermined curvature to extend in nesting relationship over said window and said shield forward edge.

18. The probe apparatus of claim 17 in which:

said collimator is formed of tungsten; and said polymeric retainer component is formed of polyphenylsulfone.

19. The probe apparatus of claim 15 in which said collimator open, cylindrical surface has an axial length of about one to two times said crystal detector forward face predetermined diameter.

20. The probe apparatus of claim 1, in which said cup-shaped window assembly is removably connected with said handle component by threaded engagement of said shield connection region with said handle connection region.

* * * * *